United States Patent [19]

Krause

[11] 3,956,381

[45] May 11, 1976

[54] METHOD FOR PREPARATION OF ETHER POLYCARBOXYLIC ACIDS

[75] Inventor: Horst-Jürgen Krause, Dusseldorf-Holthausen, Germany

[73] Assignee: Henkel & Cie G.m.b.H., Dusseldorf, Germany

[22] Filed: Oct. 21, 1974

[21] Appl. No.: 516,208

[30] Foreign Application Priority Data

Mar. 4, 1974 Austria .............................. 1758/74

[52] U.S. Cl. ........................ 260/535 P; 260/484 P
[51] Int. Cl.² ..................................... C07C 59/22
[58] Field of Search ............................... 260/535 P

[56] References Cited
FOREIGN PATENTS OR APPLICATIONS
902,359   8/1962   United Kingdom ............. 260/484 P Primary Examiner—Anton H. Sutto
Assistant Examiner—P. J. Killos
Attorney, Agent, or Firm—Hammond & Littell

[57] ABSTRACT

A process for the production of ether polycarboxylic acids comprising reacting alkali metal salts of ether carboxylic acids with carbon dioxide in the presence of (1) an alkali metal alkyl carbonate and (2) optionally, heavy metal catalysts and inert diluents at temperatures of 200°C to 350°C under pressure, acidify the resulting alkali metal salt of an ether polycarboxylic acid and recovering the ether polycarboxylic acid.

8 Claims, No Drawings

METHOD FOR PREPARATION OF ETHER POLYCARBOXYLIC ACIDS

It is known that ether polycarboxylic acids, as well as their alkali salts are good sequestering agents, particularly for the hardness-formers of water. But the practical use of these products was heretofore prevented by the fact that there was no economical production method for them. There is therefore a need for a method which permits the production of these compounds on a large technical scale.

U.S. Pat. No. 3,359,310 describes a method for the production of the potassium salt of malonic acid or malonic acid itself by the carboxylation of potassium acetate with carbon dioxide under pressure in the presence of potassium carbonate and a heavy metal catalyst at temperatures of about 300°C. However, one skilled in the art would not expect this reaction with its arduous conditions of pressure and temperature to be applied to labile ether carboxylic acids because, according to general knowledge, ethers are very easily cleaved by the action of metals at higher temperatures.

An object of the present invention is the development of a process for the production of ether polycarboxylic acids consisting essentially of reacting an alkali metal salt of an ether carboxylic acid having the formula

wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alkyl carbonate having from 1 to 4 carbon atoms in the alkyl and (2) from 0 to 30% by weight, based on the weight of the reaction mixture of a heavy metal catalyst, an alkanol having from 1 to 4 carbon atoms, a dialkyl carbonate having from 1 to 4 carbon atoms in the alkyl, a finely-divided inert diluent and an inert liquid diluent, at a temperature of between 200°C and 350°C under a pressure of at least 2 atmospheres gauge, for a time sufficient to effect carboxylation, and recovering said ether polycarboxylic acids.

This and other object of the invention will become more apparent as the description thereof proceeds.

The present invention is directed to a process for preparing ether polycarboxylic acids from the alkali metal salts of ether carboxylic acids in the presence of alkali metal alkyl carbonates by reaction with carbon dioxide at elevated temperatures and pressures.

The above objects were achieved and the problems of the prior art were overcome in that an ether carboxylic acid of the formula

where R denotes an alkyl with 1 to 22 carbon atoms, which can be straight-chain or branch-chain, and substituted by hydroxyl or carboxyl groups or interrupted by oxygen atoms, and where R' denotes hydrogen or a lower alkyl with 1 to 4 carbon atoms, is reacted in the form of its alkali metal salts in the presence of alkali metal alkyl carbonates and, optionally, heavy metal catalysts, as well as inert diluents, with carbon dioxide at temperatures of 200°C to 350°C, preferably 250°C to 300°C under pressure, preferably above 100 atmospheres gauge, and that the alkali metal salt of the ether polycarboxylic acids formed is transferred if necessary, in known manner into the free acids to give the desired ether polycarboxylic acids.

More particularly, the invention relates to a process for the production of ether polycarboxylic acids consisting of reacting an alkali metal salt of an ether carboxylic acid having the formula

wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 22 carbon atoms, and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alkyl carbonate having from 1 to 4 carbon atoms in the alkyl and (2) from 0 to 30% by weight, based on the weight of the reaction mixture of a heavy metal catalyst, an alkanol having from 1 to 4 carbon atoms, a dialkyl carbonate having from 1 to 4 carbon atoms in the alkyl, a finely-divided inert diluent and an inert liquid diluent, at a temperature of between 200°C and 350°C under a pressure of at least 2 atmospheres gauge, for a time sufficient to effect carboxylation, and recovering said ether polycarboxylic acids.

As indicated above, U.S. Pat. No. 3,359,310 gives a process for the production of potassium malonate or malonic acid by carboxylation of potassium acetate with carbon dioxide under pressure in the presence of potassium carbonate and heavy metal catalysts at temperatures of about 300°C. Application of this reaction with its adverse conditions of pressure and temperature to the labile ether carboxylic acids would seem out of the question for the man skilled in the art since, according to general knowledge, ethers are very easily split during metallization at higher temperatures.

It was completely unexpected, therefore, to find according to the invention that the alkali metal salts of the ethers of α-hydroxycarboxylic acids of the above-mentioned general formula could be carboxylated with a high yield in the presence of alkali metal alkyl carbonates, and carbon dioxide under pressure, while maintaining certain temperature conditions. The carboxylation if effected on the carbon atom in the α-position to the carboxyl group. With ether carboxylic acids which contain several carboxyl groups in the molecule, carboxylation is possible on all carbon atoms which are in α-position to carboxyl groups or on only one carbon atom which is in the adjacent or α-position to a carboxyl group. The degree of reaction of the carboxylation depends to a great extent on the selected reaction conditions.

The carboxylation of the ether carboxylic acids to be reacted takes place in the presence of alkali metal alkyl carbonate such as alkali metal methyl carbonate, according to the following reaction:

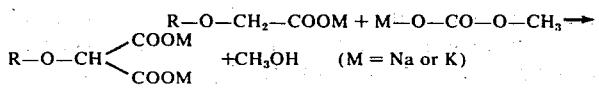

Where a dicarboxylic acid such a diglycolic acid is employed the reaction is as follows:

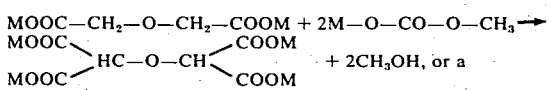

mixture of ether polycarboxylic acids are produced as follows:

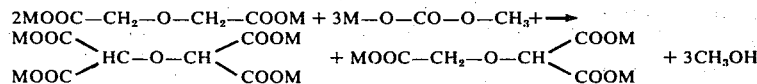

Although the reaction can take place principally without further addition of carbon dioxide, the maintainance of a certain carbon dioxide pressure is necessary for the practical realization, which pressure can vary within wide limits between 2 and 1000 atmospheres gauge, depending on the method, whether it is continuous or intermittent.

Examples of the alkali metal components of the alkali metal alkyl carbonates include sodium or potassium, preferably sodium.

The alkyl radical component of the alkali metal alkyl carbonate is derived particularly from an aliphatic alcohol having 1 to 4 carbon atoms, preferably an alkanol having 1 to 4 carbon atoms, for example, methanol, ethanol, propanol, isopropanol, n-butanol, sec.-butanol, tert.-butanol.

The alkali metal alkyl carbonate services in this reaction as a deprotonizing agent and at the same time to neutralize and stabilize the carboxyl group formed. In order to obtain good yields of ether polycarboxylic acids, it is therefore advisable to use at least the stoichiometric amount of alkali metal alkyl carbonate for the carboxyl groups present in the starting material. Preferably, however, a certain excess of alkali metal alkyl carbonate is used.

All alkali metal salts of ether carboxylic acids which meet the conditions of the above-mentioned general formula can be used as starting materials for the production of the other polycarboxylic acids according to the invention. Examples of such compounds suitable for carboxylation are the alkali metal salts of alkylglycolic acids such as methylglycolic acid, ethylglycolic acid, butylglycolic acid, laurylglycolic acid, alkyl-$C_{12-18}$-glycolic acid, also oxaalkylglycolic acids or polyoxaalkylglycolic acids such as etherification products of glycolic acids with ethylene-oxide (EO) addition products on alcohols, particularly on fatty alcohols, such as the lauryl alcohol + 2 EO ether of glycolic acid, myristic alcohol + 3 EO ether of glycolic acid, stearyl alcohol + 6 EO ether of glycolic acid; furthermore, carboxyl substituted alkylglycolic acids such as diglycolic acid, the lactic acid ether of glycolic acid, and carboxyl substituted oxaalkyl glycolic acids such as ethylene-bisglycolic acid. Primarily, the potassium and sodium salts are employed as the alkali metal salts. The alkali metal salts of the ether carboxylic acids used as starting materials for the method according to the invention should be present if possible in dry form, since it is advisable to avoid the presence of large amounts of water during the reaction. Preferably, the reaction is conducted under substantially anhydrous conditions.

The production of the alkali metal salts of the ether carboxylic acids used as starting materials in the present method can be effected according to methods known from the literature, and is not the subject of the invention.

The production of the alkali metal alkyl carbonates can be effected in a simple manner by introducing carbon dioxide, up to the saturation point, into the corresponding alcoholic alkali metal alcoholate solutions or into solutions of the alkali metal hydroxides in absolute alcohols, centrifuging off the alkali metal alkyl carbonate formed, and drying it, as described in Houben-Weyl: Methoden der Organischen Chemie (1952) Vol. 8, p. 105.

In order to obtain high yields, it is preferably to remove the alcohol formed during the reaction, continuously from the reaction mixture. For example, in the reaction in the autoclave under carbon dioxide pressure, this removal can be so conducted that the carbon dioxide pressure if released in certain intervals and the alcohol is then removed with the expelled carbon dioxide. For complete removal of the alcohol, the vessel can also be briefly evacuated. However, care must be taken that no air gets into the autoclave. Subsequently carbon dioxide is again forced into the autoclave by means of a compressor. The reaction can also be carried out continuously under pressure; however, with constant removal of the resulting alcohol by means of the carbon dioxide current. In order to avoid secondary reactions a substantial excess of carbon dioxide is preferably used.

The alkali metal salts of the ether carboxylic acids are reacted according to the invention in the presence of alkali metal alkyl carbonates with carbon dioxide under pressure. The pressure can vary within very wide limits, but should be at least 2 atmospheres gauge. The desired reaction can already be obtained with a relatively low overpressure, e.g. about 2 to 50 atmospheres. But in order to obtain good yields, it is generally desirable to utilize a carbon dioxide pressure of more than 100 atmospheres at the reaction temperature. The upper limit of the pressure is determined by the available apparatus. It can be 1000 to 2000 atmospheres or more. The pressure can be produced by corresponding pumps or compressors. In laboratory tests, liquid or solid carbon dioxide can be filled into the cooled and evacuated reaction vessel. The carbon dioxide can be recirculated, just like the other ingredients.

The reaction temperature is very critical in the present method in order to avoid decomposition of the ether carboxylic acids. In order to obtain a sufficiently rapid reaction for technical purposes, temperatures above 200°C are required. The reaction temperature, however, should not exceed 350°C if possible, unless decomposition is prevented at the same time by very high pressure. A preferred temperature range is between 250°C and 300°C. The optimum temperature depends on the desired degree of carboxylation as well as on the nature of the ether carboxylic acids used and the type of alkali metals used.

The reaction takes only a short time; but larger batches may take several hours, because of the required time for heating and cooling. Care must be taken that local overheating, which can lead to decomposition, is avoided during the heating step. For this reason, too rapid heating should be avoided. In general, a reaction time of 1 to 3 hours will be sufficient.

As it can be seen from the foregoing reaction equation, at least one mol of alkali metal alkyl carbonate is required in the reaction for each new carboxyl group to be formed. In some cases a slight excess of alkali metal alkyl carbonate is preferable. The alkali metal alkyl carbonate is preferably used as an alcohol-free, finely-divided powder. In some cases it is preferable, for a better start of the reaction, to add to the reaction mixture a small amount of a low molecular weight aliphatic alcohol, such as methanol, or diethyl carbonate. Preferably amounts of 0 to 15% by weight or 0.1% to 5% by weight, based on the weight of the reaction mixture of an alkanol having from 1 to 4 carbon atoms or a dialkyl carbonate having from 1 to 4 carbon atoms in the alkyl, are employed.

Suitable as the alkali metal alkyl carbonates are sodium methyl carbonate, potassium methyl carbonate, sodium tert.-butyl carbonate, potassium tert.-butyl carbonate, particularly sodium methyl carbonate.

Water and oxygen should be excluded, as for as possible in the present method, as in all metallo-organic synthesis, if good yields are to be obtained. If necessary, water-binding substances can be added.

Furthermore, it was found advantageous to add to the reaction mixture, inert substances with a large surface area, such as kieselguhr, finely-divided silica, powdered carbon black, and finely divided aluminum oxide, in order to improve the mechanical-physical properties of the mixture and to prevent the possible formation of lumps. The technical realization of the method is thus made considerably easier. The amount of inert additives can vary within very wide limits and is determined by the design of the apparatus used. Ordinarily, from 0 to 20% by weight, based on the weight of the reaction mixture of the finely-divided inert diluents, are employed.

Finally, the reaction can also be carried out in the presence of inert liquid diluents, such as paraffin oil. The amount of diluent is preferably so selected that a pumpable mixture is obtained. Ordinarily, from 0 to 30% by weight, based on the weight of the reaction mixture, of the inert liquid diluents are employed.

The reaction according to the invention is catalytically influenced by a number of heavy metals or heavy metal compounds. Suitable metals are, for example, iron, bismuth, zinc, nickel, copper, cadmium titanium and chromium, which can be used as such or in the form of their oxides or salts with inorganic or organic acids, such as carbonates, bicarbonates, halides, sulfates, acetates, formates, oxalates or higher fatty acid salts. Of particular advantage for the reaction according to the invention is the use of iron or zinc powder as a catalyst.

The amount of catalyst can vary within wide limits of 0 to 15% by weight, and is preferably 0.5 to 5% by weight, based on the reaction mixture, when employed.

The method can be carried out continuously or intermittently. Thus, for example, it is possible to work according to the fluidized bed method. In an intermittent operation it is advisable to use rolling autoclaves or autoclaves equipped with a stirrer as the reaction vessels. Even in the intermittent operation it is preferable to thoroughly mix the reaction material by stirring, shaking or grinding.

The reaction mixture can be worked up by dissolving the entire reaction mixture in water and filtering off the insoluble components, like the catalyst and inert additives. The ether polycarboxylic acids can be obtained from the aqueous solution by acidification with mineral acids or by treatment with a cation exchanger in acid form and subsequent working up according to the known methods.

The ether polycarboxylic acids obtained can be used with very good results as sequestering agents. In many cases, particularly for use as sequestering agents for the hardness of the water in detergents and cleaning agents, it is not necessary to produce the ether carboxylic acids in the free acid form; their alkali metal salts can be used with just as good results. In addition, the product mixtures obtained in the method according to the invention can also be used, after they have been separated from the catalyst and inert substances.

The following examples will illustrate the invention without limiting it, however, to these examples.

EXAMPLES

In the following examples, the procedure was as follows, unless indicated otherwise. The dried anhydrous starting materials were finely ground in a ball mill and heated in a high-pressure autoclave of 500 ml capacity under carbon dioxide pressure.

The "initial pressure" was the carbon dioxide pressure in the autoclave before the commencing heating. This pressure was adjusted in each case at 50°C, in view of the critical temperature of carbon dioxide. The "end pressure" was the maximum pressure observed at the corresponding reaction temperature.

In many cases the autoclave was provided with a glass insert or partial lining. This is indicated in the respective tests.

For the working up of the reaction mixture, the crude product was dissolved in water and filtered hot. After cooling, the filtrate was mixed under stirring with a particulated cation exchange resin in acid form in order to acidify the product, whereby the carbon dioxide could escape without foaming. Subsequently the ion-exchange resin was filtered off and the aqueous solution of the ether polycarboxylic acids was conducted through a fresh cation exchange resin column in the acid form, in order to transform it completely into the free acid. The eluate was evaporated under vacuum until dry. The total yield of the ether polycarboxylic acids obtained this way corresponds to the analytical composition of the reaction mixtures.

The analytical composition of the ether polycarboxylic acids obtained was determined by gas chromatography of the methyl esters after esterification of the acids with diazomethane to the methyl esters. The usual analytical data were determined from the pure single fractions obtained by distillation or gas chromatography.

In the following tables of the following example, the individual abbreviations have the following meanings:

init. pressure = the initial carbon dioxide pressure in atmospheres measured at 50°C.
E-pressure = the end carbon dioxide pressure at the respective reaction temperature.
temo. = the reaction temp. in °C, measured in vapor area.
com. TC% = the percent composition of total carboxylic acids in %
DG = diglycolic acid
MDG = methyl diglycolic acid
MOA = methoxyacetic acid
DOA = dodecyloxyacetic acid CMT = carboxymethyl tartronic acid (2-oxa-propane-1,1,3-tricarboxylic acid)
DT = ditartronic acid (2-oxa-1,1,3,3-tetracarboxylic acid)
OBT = 2-oxa-butane-1,1,3-tricarboxylic acid
MA = malonic acid
MOM = methoxymalonic acid
DOM = dodecyloxymalonic acid
B = by-products In the examples marked "x" the alcohol formed was removed after 2 hours reaction time by discharging the carbon dioxide. Subsequently a pressure of 150 atmospheres gauge was set with fresh carbon dioxide at 250°C to 260°C, and the reaction was completed during the course of another hour at the indicated temperature.

EXAMPLES 1 to 3 (Glass Insert)

Batch:
21.0 gm of dipotassium salt of diglycolic (0.1 mol)
14.7 gm of sodium methyl carbonate (0.15 mol)
4.0 gm Aerosil
The heating time at the reaction temperature is indicated in hours at the respective temperature.

The results of the tests are compiled in Table I below.

TABLE I

| Example | Init.Press. | End Press. | Temp. °C | Comp. TC% |
|---|---|---|---|---|
| 1x | 270 | 950/2h 200/1h | 270 | 44.3DG;44.5CMT; 6.0DT;5.2MA+B |
| 2 | 270 | 830/1h | 270 | 58.8DG;32.9CMT; 5.5DT;2.8 MA+B |
| 3x | 270 | 840/2h 170/1h | 250 | 54.4DG;38.5CMT; 5.8DT;1.3MA+B |

EXAMPLE 4

Batch:
17.8 gm of disodium salt of diglycolic acid (0.1 mol)
14.7 gm of sodium methyl carbonate (0.15 mol)
4.0 gm Aerosil
Heating time: 3 hours at reaction temperature. The test results are compiled in Table II below.

TABLE II

| Example | Init.Press. | End Press. | Temp°C. | Comp. TC% |
|---|---|---|---|---|
| 4x | 270 | 800/2h 180/1h | 270 | 56.1DG;33.0CMT; 10.9 MA+B |

EXAMPLE 5

Batch:
21.0 gm of dipotassium salt of diglycolic acid (0.1 mol)
23.4 gm of potassium butyl carbonate (0.15 mol)
4.0 gm of Aerosil
The test results are compiled in Table III below.

TABLE III

| Example | Init.Press. | End Press. | Temp.°C | Comp. TC% |
|---|---|---|---|---|
| 5x | 270 | 1060/2h 200/1h | 270 270 | 26.8DG;52.8CMT; 14.0DT;6.4 MA+B |

EXAMPLE 6

Batch:
21.0 gm of dipotassium salt of diglycolic acid (0.1 mol)
21.0 gm of sodium butyl carbonate (0.15 mol)
4.0 gm of Aerosil
The test results are compiled in Table IV below.

TABLE IV

| Example | Init.Press. | End Press. | Temp.°C | Comp. TC % |
|---|---|---|---|---|
| 6x | 270 | 700/2h 180/1h | 270 270 | 47.5DG;42.2 CMT; 4.1DT;6.2 MA+B |

EXAMPLE 7

Batch:
21.0 gm of dipotassium salt of diglycolic acid (0.1 mol)
17.0 gm of dipotassium methylcarbonate (0.15 mol)
4.0 gm of Aerosil
The test results are compiled in Table V below.

TABLE V

| Example | Init.Press. | End Press. | Temp.°C. | Comp. TC % |
|---|---|---|---|---|
| 7x | 300 | 770/2h | 270 | 41.4DG;43.7CMT; |

TABLE V-continued

| Example | Init.Press. | End Press. | Temp.°C. | Comp. TC % |
|---|---|---|---|---|
| | | 190/1h | 270 | 6.8DT;8.1MA+B |

EXAMPLE 8

Batch:
21.0 gm of dipotassium salt of diglycolic acid (0.1 mol)
23.4 gm of potassium tert.-butyl carbonate (0.15 mol)
4.0 gm of Aerosil The test results are compiled in Table VI below.

TABLE VI

| Example | Init.Press | End Press | Temp°C | Comp. TC % |
|---|---|---|---|---|
| 8* | 270 | 880/2h | 270 | 42.8DG; 42.3CMT; |
| | | 190/1h | 270 | 8.9DT; 6.0MA+B |

EXAMPLE 9

Batch:
21.0 gm of dipotassium salt of diglycolic acid (0.1 mol)
14.7 gm of sodium methyl carbonate (0.15 mol)
4.0 gm of Aerosil This test was carried out in the absence of carbon dioxide. For setting comparable pressure conditions, a nitrogen pressure of 50 atmospheres gauge was first set at 50°C. After 2 hours reaction time, the gas was discharged and replaced by fresh nitrogen of 50 atmospheres gauge at 260°C. The results of this test are compiled in Table VII below.

TABLE VII

| Init.Press. | End Press. | Temp.°C | Comp.TC % |
|---|---|---|---|
| 50 | 180/2h | 270 | 85.0 DG; 10.8CMT; |
| | 60/1h | 270 | 4.2 MA+B |

EXAMPLE 10

Batch:
23.5 gm of dipotassium salt of methyl diglycolic acid (0.1 mol)
23.4 gm of potassium butyl carbonate (0.15 mol)
4.0 gm of Aerosil
The test results are compiled in Table VIII below.

TABLE VIII

| Example | Init.Press. | End Press. | Temp.°C | Comp. TC % |
|---|---|---|---|---|
| 10* | 270 | 890/2h | 270 | 63.5 MDG;29.90BD; |
| | | 180/1h | 270 | 6.6 B |

EXAMPLE 11

Batch:
3.5 gm of potassium of methoxyacetic acid (0.027 mol)
5.6 gm of potassium butyl carbonate (0.04 mol)
1.1 gm of Aerosil
The test results are compiled in Table IX below.

TABLE IX

| Example | Init.Press. | End Press. | Temp.°C | Comp. TC % |
|---|---|---|---|---|
| 11* | 270 | 970/2h | 270 | 50.1MOA;37.6MOM: |
| | | 190/1h | 270 | 12.3 B |

EXAMPLE 12

Batch:
12.8 gm of potassium salt of methoxyacetic acid (0.1 mol)
21.0 gm of sodium butyl carbonate (0.15 mol)
4.0 gm of Aerosil
The results of this test are compiled in Table X below.

TABLE X

| Example | Init.Press. | End Press. | Temp.°C | Comp. TC % |
|---|---|---|---|---|
| 12* | 270 | 910/2h | 270 | 66.6MOA;20.7MOM; |
| | | 190/1h | 270 | 12.7 B |

EXAMPLE 13

Batch:
14.1 gm of potassium salt of dodecyloxyacetic acid (0.05 mol)
8.6 gm of potassium methyl carbonate (0.075 mol)
3.0 gm of Aerosil
The test results are compiled in TAble XI below.

TABLE XI

| Example | Init.Press. | End Press. | Temp. °C | Comp. TC % |
|---|---|---|---|---|
| 13* | 270 | 750/2h | 270 | 89.9DOA;9.5DOM; |
| | | 160/1h | 270 | 0.6 B |

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A process for the production of ether polycarboxylic acids consisting essentially of reacting an alkali metal salt of an ether carboxylic acid having the formula

R — O — CHR' — COOH wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alkyl carbonate having from 1 to 4 carbon atoms in the alkyl and (2) from 0 to 30% by weight, based on the weight of the reaction mixture of a heavy metal catalyst, an alkanol having 1 to 4 carbon atoms, a dialkyl carbonate having from 1 to 4 carbon atoms in the alkyl, a finely-divided inert diluent and an inert liquid diluent, at a temperature of between 200°C and 350°C under a pressure of at least 2 atmospheres gauge, for a time sufficient to effect carboxylation, and recovering said ether polycarboxylic acids.

2. The process of claim 1, wherein said temperature ranges between 250°C and 300°C.

3. The process of claim 1, wherein said alkali metal alkyl carbonate is sodium alkyl carbonate having from 1 to 4 carbon atoms in the alkyl.

4. The process of claim 1, wherein said alkali metal alkyl carbonate is sodium methyl carbonate.

5. The process of claim 1, wherein said reaction is conducted under substantially anhydrous conditions in the substantial absence of oxygen.

6. The process of claim 1, wherein the alcohol formed during the reaction is intermittently removed from the reaction mixture.

7. The process of claim 1, wherein from 0 to 15% by weight, based on the reaction mixture, of a compound selected from the group consisting of an alkanol having from 1 to 4 carbon atoms and a dialkyl carbonate having from 1 to 4 carbon atoms in the alkyl, is added to the reaction mixture.

8. The process of claim 1, wherein said ether polycarboxylic acid is carboxymethyl tartronic acid and wherein said ether carboxylic acid is diglycolic acid.

* * * * *